(12) United States Patent
Tan

(10) Patent No.: US 8,166,578 B2
(45) Date of Patent: May 1, 2012

(54) GOGGLE WITH QUICK RELEASE DOUBLE LOCKING LENS

(75) Inventor: William Tan, Los Angeles, CA (US)

(73) Assignee: Kingman International Corporation, Baldwin Park, CA (US)

( * ) Notice: Subject to any disclaimer, the term of this patent is extended or adjusted under 35 U.S.C. 154(b) by 565 days.

(21) Appl. No.: 12/401,561

(22) Filed: Mar. 10, 2009

(65) Prior Publication Data

US 2010/0229292 A1 Sep. 16, 2010

(51) Int. Cl.
*A61F 9/02* (2006.01)

(52) U.S. Cl. .............................................. 2/427

(58) Field of Classification Search ............... 2/410, 6.3, 2/6.7, 425, 427, 428, 430, 417, 418, 9, 426, 2/448

See application file for complete search history.

(56) References Cited

U.S. PATENT DOCUMENTS

| | | | | |
|---|---|---|---|---|
| 4,977,627 A * | 12/1990 | Metcalfe et al. | ............ | 2/437 |
| 5,410,763 A * | 5/1995 | Bolle | ............ | 2/436 |
| 5,617,588 A * | 4/1997 | Canavan et al. | ............ | 2/428 |
| 5,915,540 A * | 6/1999 | Chou | ............ | 2/428 |
| 6,047,410 A * | 4/2000 | Dondero | ............ | 2/426 |
| 6,105,177 A * | 8/2000 | Paulson et al. | ............ | 2/431 |
| 6,276,795 B1 * | 8/2001 | Hall et al. | ............ | 351/62 |
| 6,381,749 B1 * | 5/2002 | Cyr | ............ | 2/9 |
| 6,611,965 B1 * | 9/2003 | Lee | ............ | 2/431 |
| 6,948,813 B2 * | 9/2005 | Parks | ............ | 351/158 |
| 7,003,802 B2 * | 2/2006 | Broersma | ............ | 2/9 |
| 7,320,144 B2 * | 1/2008 | Katz et al. | ............ | 2/9 |
| 7,725,959 B2 * | 6/2010 | Wang-Lee | ............ | 2/428 |
| RE41,834 E * | 10/2010 | Parks | ............ | 351/158 |
| 7,895,679 B2 * | 3/2011 | Takeshi et al. | ............ | 2/448 |
| 7,895,680 B2 * | 3/2011 | Anderson | ............ | 2/452 |
| 8,011,026 B2 * | 9/2011 | Stevens | ............ | 2/427 |

* cited by examiner

*Primary Examiner* — Danny Worrell
(74) *Attorney, Agent, or Firm* — Blakely, Sokoloff, Taylor & Zafman LLP

(57) ABSTRACT

An apparatus for releasably locking a protective eye lens to the housing of a protective face cover is disclosed. The apparatus is configured to have an inner and outer lock. The inner lock couples the protective eye lens to the housing. The inner lock can release the protective eye lens from the housing through the use of a release unit. An activator on the release unit is guarded by the outer lock to prevent inadvertent movement of the activator and consequent unintended release of the protective eye lens from the housing.

7 Claims, 3 Drawing Sheets

GOGGLE WITH QUICK RELEASE DOUBLE LOCKING LENS

BACKGROUND

1. Field of the Invention

Embodiments of the present invention relate to an apparatus for securing a lens to a housing. Specifically, the embodiments of the present invention relate to an apparatus with a dual locking mechanism where the multiple locks ensure that the lens is not inadvertently released from the housing.

2. Description of the Related Art

Eye protection is a critical concern for many individuals. Based on this concern, devices have been developed to shield the eyes of a person from particulates, water, chemicals, and various other items which can cause harm to the sensitive components of an eye. These eye protection apparatuses often include a mask with an attached lens to guard the eyes of a wearer. Firemen, paintball participants, and welders each wear masks with an attached lens to protect their eyes from foreign objects. Typically, the attached lens can be released from the mask with the aid of tools. During fast-paced activities, the time associated with using tools to remove a lens from a mask is prohibitively long.

To address the need for a quicker release of the lens from a mask, quick release single locking mechanisms have been used to attach the lens to the mask. However, use of quick release single locking mechanisms often results in inadvertent release of the lens from the housing. For example, a paintball traveling at a high-rate of speed can strike an unprotected single locking mechanism. The force of the paintball could disengage the lock and consequently release the lens from the mask. This premature release of the lens risks damage to the eyes of the user because without the lens the eyes of the user are exposed to foreign objects.

BRIEF DESCRIPTION OF THE DRAWINGS

The invention is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

DETAILED DESCRIPTION

Figure 1:
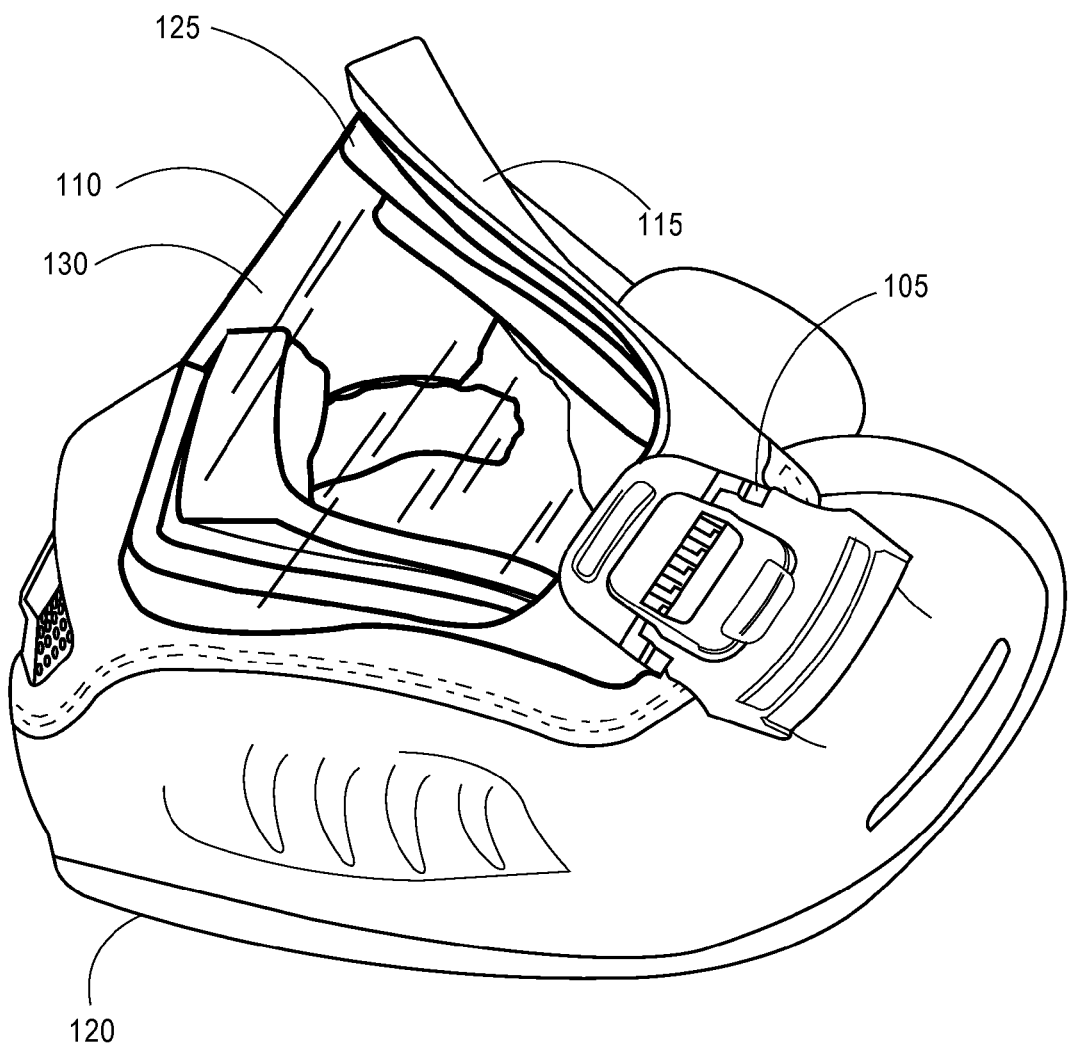
FIG. 1 is a diagram of one embodiment of a quick release double locking mechanism attaching a lens to a paintball helmet.

FIG. 1 is a diagram of one embodiment of a paintball mask 100 which is composed of a double locking mechanism 105, a protective eye lens 110, a housing 115, and a protective cover 120. The paintball mask 100 is designed to fit snuggly around the head of a wearer such that the protective eye lens 110 covers the eyes of the wearer.

Although the embodiment in FIG. 1 is a paintball mask, any apparatus designed to receive a protective eye lens 110 can be used with the double locking mechanism 105. In alternate embodiments, a hockey helmet with an eye shield, ski goggles, a football helmet with an eye shield, or similar articles that include a releasable shielding component can include the double locking mechanism 105. The paintball mask 100 is intended as an example and not as a limitation.

The housing 115 acts as a protective face cover to shield the head of a wearer from projectiles. The housing 115 defines an opening 130. The shape or perimeter of the opening 130 complements the protective eye lens 110. The opening 130 creates a viewing area for the wearer. When the head of a wearer is placed in the housing 115, the eyes of the wearer are aligned with the center of the opening 130 such that the wearer can see out of the opening 130. In one embodiment, the housing 115 is contoured to the dimensions of the head of a wearer such that the housing 115 can receive the head of a wearer.

The housing 115 includes a mounting component 125 to receive the protective eye lens 110. In one embodiment, the portion of the housing 115 around the opening 130 forms a recessed slot which defines the mounting component 125. The slot is capable of receiving the outer edge of the protective eye lens 110 such that the protective eye lens 110 is cradled by the housing 115. The slot is sized to adequately support the protective eye lens 110, but does not block visibility of the wearer. In one embodiment, the protective eye lens 110 includes a ridge along the outer edge. The ridge fits within the slot of the housing 115 such that the protective eye lens 110 is securely held by the housing 115 and forms a seal between the protective eye lens 110 and the housing 115. Further, the seal prevents particles and objects that are hazardous to the eyes of a wearer from seeping through the mask 100 and being exposed to the eyes of a wearer.

In one embodiment, the housing 115 is composed of a hard impact resilient material. The housing 115 can be formed of materials including, but not limited to, plastics (e.g., polyethylene, polycarbonate, polypropylene, polystyrene, or acrylonitrile butadiene styrene), metals (e.g., aluminum, steel, tin, titanium, or chrome), composite compounds (e.g., carbon fiber or fiberglass), and other rigid materials.

In one embodiment, the interior of the housing 115 is padded. The padding creates a barrier between the head of the wearer and the impact resilient material. The padding can be formed of materials including, but not limited to, foam, cotton, down, felt, and other similar materials. In one embodiment, the housing 115 includes a series of holes that provide ventilation for the head of a wearer. In one embodiment, the holes are provided in the portion of the housing 115 covering the mouth of the wearer. The holes provide ventilation for the head of the wearer without exposing the eyes.

In one embodiment, a protective cover 120 is coupled to the housing 115. The protective cover 120 is sized to protect the neck and ears of a wearer. The protective cover 120 is impact resistant and accordingly protects the wearer from the impact of a high velocity projectile, such as a paintball. The protective cover 120 is coupled to the housing 115 through techniques including, but not limited to, adhesives, stitching, fasteners, and similar methods. The protective cover 120 can be formed of materials including, but not limited to, foam, cotton, down, felt, and other similar materials. In one embodiment, the protective cover 120 is entirely covered with a fabric.

The protective eye lens 110 is a transparent shield which is coupled to the housing 115. The protective eye lens 110 guards the eyes of a wearer from projectiles, dust, and other items hazardous to the eyes of a wearer. In one embodiment, the protective eye lens 100 is curved to the dimensions of an opening 130 in the housing 115. The curved protective eye lens 110 allows both direct forward vision as well as peripheral vision to a wearer.

Figure 2:
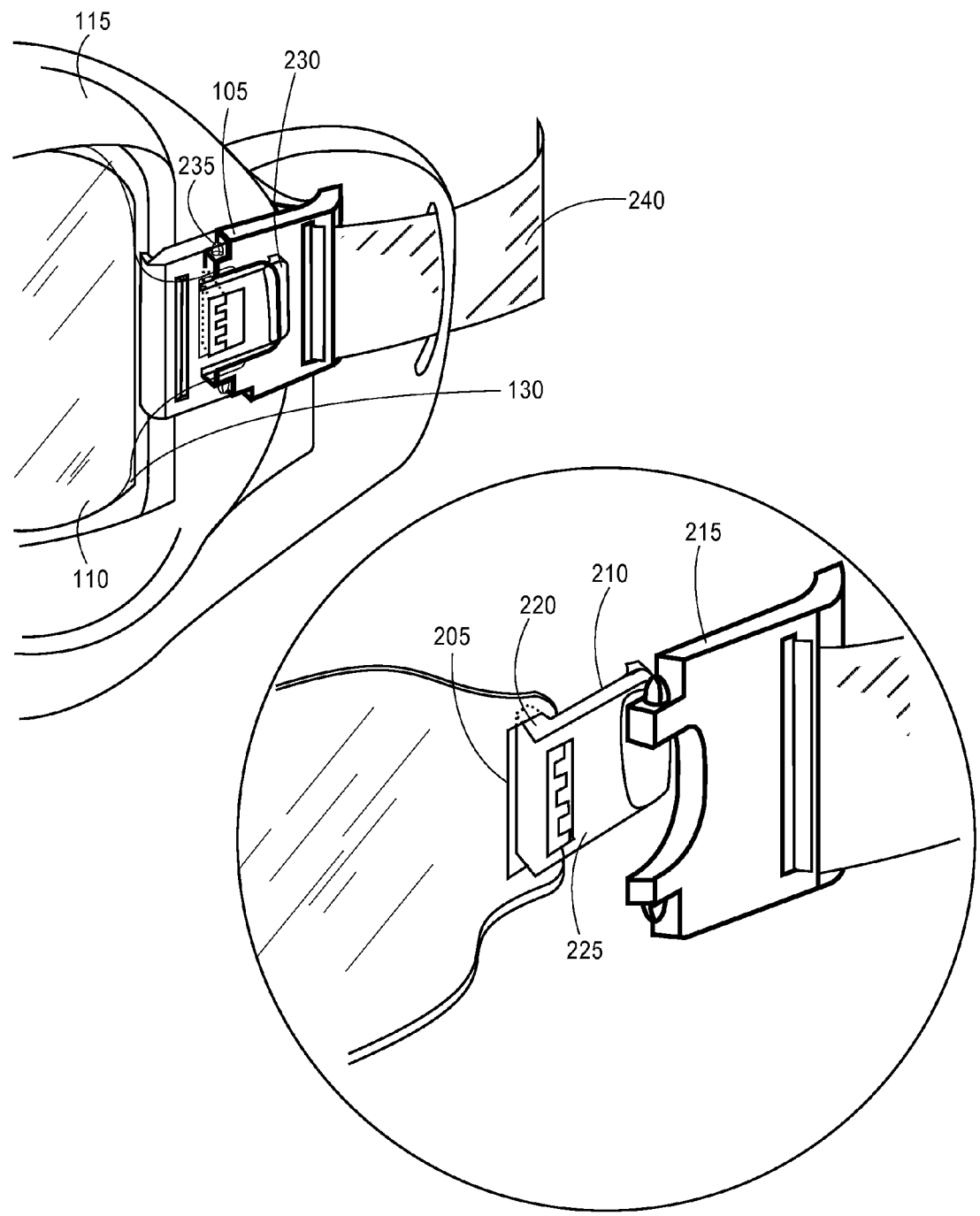
FIG. 2 is a diagram of one embodiment of a double locking mechanism releasably attaching a protective eye lens to a housing.

FIG. 2 is a diagram of one embodiment of a double locking mechanism 105 releasably attaching a protective eye lens 110 to a housing 115. The protective eye lens 110 includes a set of receiving units 205. A "set" as used herein, refers to any positive whole number of items including one item. In one embodiment, the receiving unit 205 defines slits on the edges of the protective eye lens 110. The protective eye lens 110 can be formed of materials including, but not limited to, polyethylene, polycarbonate, polypropylene, polystyrene, acrylonitrile butadiene styrene or other transparent impact resistant materials.

The protective eye lens 110 is releasably attached to the housing 115 through the use of an attachment mechanism. In one embodiment, the attachment mechanism is a double locking mechanism 105. When engaged, the double locking mechanism 105 firmly holds the protective eye lens 110 to the housing 115. The double locking mechanism 105 can be disengaged by a wearer. Upon disengagement of the double locking mechanism 105, the protective eye lens 110 can be removed by the wearer from the housing 115 without the use of tools. In one embodiment, the dimensions and shape of the double locking mechanism 105 allow a wearer to operate the double locking mechanism 105 with a single hand.

The double locking mechanism 105 is comprised of an inner lock 210 and an outer lock 215. In one embodiment, the inner lock 210 is coupled to the housing 115 and the outer lock 215 is coupled to the inner lock 210 via a coupling mechanism 235. In another embodiment, both the inner lock 210 and outer lock 215 are separately coupled directly to the housing 115.

In one embodiment, the coupling mechanism 235 is defined by a joint. The outer lock 215 is attached to the inner lock 210 at the joint such that the outer lock 215 pivots about the inner lock 210. The joint can define a revolute joint (e.g. a "pin" and "hinge"), cylindrical joint, screw joint, spherical joint ("ball and socket"), or similar joint apparatus. The joint permits the outer lock 215 to pivot from a first position, in which the release unit 225 is covered, and a second position, in which the release unit 225 is exposed. Conversely, the joint permits the outer lock 215 to pivot from the second position to the first position.

In one embodiment, an adjustable strap 240 is attached to at least one outer lock 215. The adjustable strap 240 firmly holds the housing 115 to the head of a wearer. In one embodiment, a first end of the adjustable strap is attached to an outer lock 215 through slots in the outer lock 215. In one embodiment, the adjustable strap 240 is connected to the outer lock 215 by being weaved through slots on the outer lock 215. In other embodiments, the adjustable strap 240 is connected to the outer lock 215 through use of fasteners, adhesives, or other binding techniques. In one embodiment, the second end of the adjustable strap 240 is connected to another outer lock 215. In other embodiments, the second end is connected to the housing 115. A different technique from that used to connect the first end of the adjustable strap 240 can be employed to connect the second end of the adjustable strap 240.

The adjustable strap 240 creates a secure frictional fit between the head of the wearer and the housing 115. In one embodiment, when the strap 240 becomes tense the adjustable strap 240 firmly holds the outer lock 215 in a first position. In the first position, the outer lock 215 covers the release unit 225 such that it cannot be accessed or activated by a wearer or foreign object while the strap 240 is tense. After the tension has been removed from the adjustable strap 240, the outer lock 215 can be moved into a second position such that the release unit 225 can be accessed and manipulated.

The adjustable strap 240 can employ any adjusting mechanism that adjusts the length of a strap, for example a ratchet and pawl. In one example embodiment, the adjustable strap 240 defines a perforated or ratcheted portion to enable incremental adjustment of the length of the adjustable strap 240. The length of the adjustable strap 240 can be adjusted to conform to the size of the head of the wearer. In one example embodiment, the adjustable strap 240 includes two straps connected at an adjusting mechanism and the length can be between ten to fifteen inches when adjusted. The width of the adjustable strap 240 can be any size and is not necessarily uniform. This allows the adjustable strap 240 to be adjusted to any wearer as a one size fits all structure. In one example embodiment, the width of the adjustable strap 240 can be between 0.4 to 2 inches. In another embodiment, the adjustable strap 240 does not have an adjusting mechanism and, instead, the adjustable strap 240 is a U-shaped plastic or metal strap capable of pushing the mask 100 towards the head of a wearer.

The adjustable strap 240 can be formed wholly or partially of materials including, but not limited to, flexible plastics, foam, synthetic polymers, cotton, or similar materials that are capable of creating a secure frictional fit between the head of the wearer and the housing 115.

As shown in FIG. 2, the inner lock 210 includes a clasp 220 and a release unit 225. The clasp 220 releaseably joins the protective eye lens 110 and the housing 115. The inner lock 210 acts as a connector to directly couple the protective eye lens 110 to the housing 115.

To firmly attach the protective eye lens 110 to the housing 115, the clasp 220 engages a receiving unit 205 of the lens 110. Accordingly, the clasp 220 and receiving unit 205 are complimentarily shaped and sized such that they interlock when engaged. In one embodiment, the clasp 220 and receiving unit 205 define a tongue and groove. Both the tongue and the groove are beveled such that they form an interlocking connection which firmly holds the protective eye lens 110 to the housing 115. In another embodiment, the clasp 220 and receiving unit 205 define a snap type connector. In still another embodiment, the clasp 220 and receiving unit 205 define a hook-and-loop fastener. It should be noted that other embodiments can implement other known connecting device to releasably connect the protective eye lens 110 to the housing 115.

In one embodiment, the inner lock 210 includes a hook to couple the inner lock 210 to the housing 115. The hook is coupled to the release unit 225 of the inner lock 210. The hook engages an edge of the housing 115 such that the inner lock 210 is firmly connected to the housing 115. In other embodiments, the inner lock 210 is coupled to the housing 115 with an adhesive including, but not limited to, elastomers, thermoplastics, thermosettings, neoprene and similar compounds. In still other embodiments, the inner lock 210 is part of the housing 115 and is molded from the same impact resistant material. These methods of coupling the inner lock to the housing are exemplary. Other attachment mechanisms can be used in place of those described.

In one embodiment, the housing 115 forms an overlap section that creates a pocket to receive the protective eye lens 110. The receiving unit 205 of the protective eye lens 110 can be placed in the pocket. In this embodiment, the inner lock 210 is coupled to a center portion of the overlap such that the inner lock 210 it is aligned with the receiving unit 205 of the protective eye lens 110.

A portion of the release unit 225 defines an activator 230. Movement of the activator 230 causes the release unit 225 to move. Upon movement of the release unit 225, the clasp 220 disengages the receiving unit 205 of the protective eye lens 110 and the protective eye lens 110 is released from the housing 115.

The outer lock 215 forms a guard to prevent movement of the activator 230. The outer lock 215 is sized such that it can cover the activator 230 to prevent access. Covering the activator 230 prevents accidental movement of the release unit 225 and consequent release of the protective eye lens 110.

Accidental movement of the release unit 225 and release of the protective eye lens 110 could potentially cause severe eye damage by leaving the eyes of a wearer exposed to harmful projectiles or contaminants.

In one embodiment, the double locking mechanism 105 is located on the exterior of the housing 115. Exterior of the housing as used herein refers to the side of the housing 115 opposite the side that is in contact with the head of the wearer. Placement of the double locking mechanism 105 on the exterior of the housing 115 provides easier access to the double locking mechanism 105 by a wearer.

The inner lock 210 and outer lock 215 can be formed of materials including, but not limited to, plastics (e.g., polyethylene, polycarbonate, polypropylene, polystyrene, or acrylonitrile butadiene styrene), metals (e.g., aluminum, steel, tin, titanium, or chrome), composite compounds (e.g., carbon fiber or fiberglass), and other rigid materials. The inner lock 210 and outer lock 215 can be formed by molding, extrusion or similar techniques FIGS. 3A, 3B, 3C, and 3D are diagrams of a cross-sectional view of one embodiment of an inner lock 210 and outer lock 215 attaching a protective eye lens 110 to a housing 115. FIGS. 3A, 3B, 3C, and 3D depict the steps taken to release the protective eye lens 110 from the housing 115 by deactivating the quick release double locking mechanism 105. In the embodiment shown in FIGS. 3A, 3B, 3C, and 3D, the release unit 225 of the inner lock 210 comprises a rectangular lever with a rectangular tab attached to an end of the lever. The tab defines the activator 230. The clasp 220 is coupled to the release unit 225 at a center section of the release unit 225. The outer lock 215 forms a curved structure that creates a dome around the activator 230.

Figure 3A:
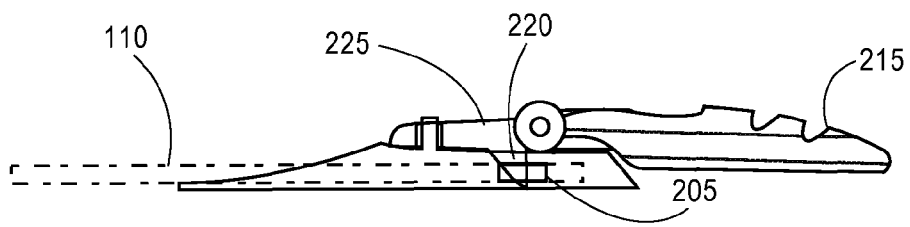
FIGS. 3A, 3B, 3C, and 3D are diagrams of a cross-sectional view of one embodiment of a quick release double locking mechanism attaching a lens to a housing.

In FIG. 3A, the outer lock 215 is in a first position such that the outer lock 215 covers the activator 230. In the first position, the outer lock 215 firmly covers the activator 230 such that the force from a projectile, such as a high velocity paintball, will not move the activator 230. Preventing movement of the activator 230 by the outer lock 215 inhibits movement of the release unit 225. Inhibiting movement of the release unit 225 prevents disengagement of the clasp 220 from the receiving unit 205 and thus prevents inadvertent release of the protective eye lens 110.

Figure 3B:
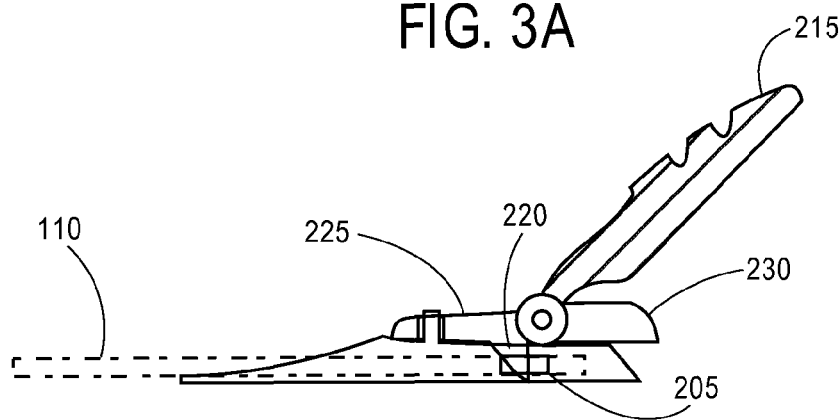

In FIG. 3B, the outer lock 215 is in a second position. In this second position the activator 230 is exposed. Exposure of the activator 230 allows access to move the activator 230 in a range of directions. For example, the release unit 225 can be rotated away and consequently cause the clasp 220 to disengage the receiving unit 205 of the protective eye lens 110.

Figure 3C:
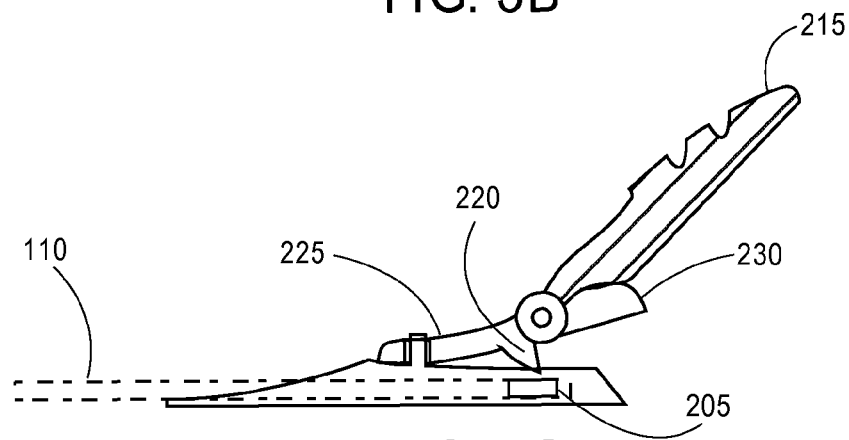

In FIG. 3C, a force has been applied to the activator 230 of the release unit 225. Consequently, the release unit 225 moves in a first direction parallel to the force applied to the activator 230. Movement of the release unit 225 in a first direction causes the clasp 220 to move in the same direction and thereby moves the clasp 220 away from the receiving unit 205 of the protective eye lens 110. Moving the clasp 220 away from the receiving unit 225 disconnects the clasp 220 from the receiving unit 205 and the protective eye lens 110 is free to be removed from the housing 115. In one embodiment, movement of the activator 230 1 to 5 degrees from the position of the activator 230 in FIG. 3B disconnects the clasp 220 from the receiving unit 205.

In one embodiment, multiple sets of double locking mechanisms 105 are used to secure the protective eye lens 110 to the housing 115. In this embodiment, each of the double locking mechanisms 105 would need to be disconnected from the protective eye lens 110 prior to removing the protective eye lens 110 from the housing 115. Using multiple double locking mechanisms 105 better ensures the protective eye lens 110 is firmly fastened to the housing 115.

Figure 3D:
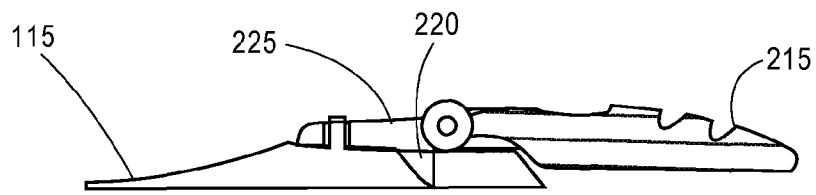

In FIG. 3D, the protective eye lens 110 is removed from the housing 115 by pulling the protective eye lens 110 away from the housing 115 that it was previously detached from. A force has been applied to the activator 230 to move the release unit 225 and the clasp 220 to their original position in FIG. 3A and FIG. 3B.

In one embodiment, the release unit 225 and clasp 220 are automatically moved to their positions in FIG. 3D after force is no longer applied to the activator 230. Automatic movement is caused by tension in the release unit 225 which is opposite in direction to the force originally applied to the activator 230. Discontinuation of the applied force causes the release unit 230 and clasp 220 to move in the direction dictated by the tension. In alternate embodiments, springs, elastics or similar devices are used to perform automatic movement.

In the foregoing specification, the invention has been described with reference to specific embodiments thereof. It will, however, be evident that various modifications and changes can be made thereto without departing from the broader spirit and scope of the invention as set forth in the appended claims. The specification and drawings are, accordingly, to be regarded in an illustrative rather than a restrictive sense.

What is claimed is:

1. An apparatus comprising:
a housing forming a protective face cover;
a lens removably coupled to the housing, the lens forming a protective eye cover; and
an attachment mechanism to removably secure the lens to the housing, the attachment mechanism to enable a quick release of the lens from the housing, the attachment mechanism comprising an outer fastener and an inner fastener, the outer fastener moveable between a first position that restricts access to the inner fastener and a second position; and
a clasp to engage the lens, the clasp coupling the lens to the housing; and a lever to release the lens from the housing.

2. The apparatus of claim 1, wherein the lens comprises:
a receiving unit to receive the clasp.

3. The apparatus of claim 1, wherein the attachment mechanism is coupled to the exterior of the housing.

4. An apparatus comprising:
a housing forming a protective face cover;
a lens removably coupled to the housing, the lens forming a protective eye cover; and
an attachment mechanism to removably secure the lens to the housing, the attachment mechanism to enable a quick release of the lens from the housing, the attachment mechanism comprising an outer fastener and an inner fastener, the outer fastener moveable between a first position that restricts access to the inner fastener and a second position; and
a coupling mechanism to couple the outer fastener to the inner fastener.

5. The apparatus of claim 4, further comprising:
a strap coupled to the outer fastener, the strap to secure the housing to the head of a user.

6. The apparatus of claim 4, further comprising
a joint to couple the inner fastener to the outer fastener such that the outer fastener pivots about the inner fastener.

7. The apparatus of claim 1, wherein the protective face cover is a paintball mask.

* * * * *